US007993262B2

(12) United States Patent
Cianfrani

(10) Patent No.: US 7,993,262 B2
(45) Date of Patent: Aug. 9, 2011

(54) STIMULATORY DEVICE SUPPORT APPARATUS

(75) Inventor: Marcus Frank Cianfrani, Berlin, NJ (US)

(73) Assignee: Cianfrani Holding, LLC, Berlin, NJ (US)

( * ) Notice: Subject to any disclaimer, the term of this patent is extended or adjusted under 35 U.S.C. 154(b) by 1140 days.

(21) Appl. No.: 11/371,699

(22) Filed: Mar. 9, 2006

(65) Prior Publication Data

US 2007/0213772 A1 Sep. 13, 2007

(51) Int. Cl.
*A61F 5/00* (2006.01)

(52) U.S. Cl. ........................................................ 600/38

(58) Field of Classification Search .............. 600/38–41; 601/97–112, 116, 122, 126, 128, 57, 58, 601/49; 5/633, 457, 449, 461, 652, 653, 5/655.4, 655.9, 656, 657, 657.5, 929; 297/452.41, 297/156, 175–179, 188.01, 188.14, 195.1, 297/188.21, 217.1, 217.3, 461, 462, 463.2; 128/845

See application file for complete search history.

(56) References Cited

U.S. PATENT DOCUMENTS 4,718,727 A * 1/1988 Sheppard ................. 297/452.26
5,580,132 A * 12/1996 Rediske ................... 297/452.41
6,038,719 A * 3/2000 Castagna .......................... 5/636
6,142,929 A * 11/2000 Padgett ........................... 600/38
6,814,709 B2 * 11/2004 Schwartz et al. ............... 601/57

OTHER PUBLICATIONS

Leather & Chrome Toys, "Joystick with Vibrator", http://leatherandchrometoys.com/products/402.html , 2 pages (2005).
Fantazma Erotic Gifts, "California Exotic: Joystick with Vibrator", http://www.fantazma.com/Detail.tpl?cart=318631091612768&SKU=0499-00-3, 1 page (2005).
BedBuddyonline "The Amazing BedBuddy!" http://bedbuddyonline.com, KTM Enterprises, LLC, 1 page (2005).

* cited by examiner

*Primary Examiner* — Samuel G Gilbert
(74) *Attorney, Agent, or Firm* — Flaster/Greenberg PC

(57) ABSTRACT

Disclosed is an apparatus for supporting a stimulatory device. Such device eliminates the need for a user to manually hold and/or position such stimulatory device. Rather, such device remains in a stationary position, and a user may adjust her position relative to the stimulatory device and the supporting apparatus. In one aspect of the present invention, a seat is provided upon which a user may lie, rest, or otherwise support herself. In another aspect of the present invention, the apparatus is manufactured from a yielding material to provide ease of use and comfort while simultaneously minimizing the possibility of abrasions, injuries, and the like. In yet another aspect of the present invention, a height of the stimulatory device above an upwardly facing surface of the stimulatory device is adjustable by a user. Finally, such device may be used during masturbation, during sexual intercourse, and/or for treatment of sexual dysfunction.

30 Claims, 5 Drawing Sheets

100

100

STIMULATORY DEVICE SUPPORT APPARATUS

BACKGROUND OF THE INVENTION

Embodiments of the present invention generally relate to apparatus for efficiently and effectively supporting a stimulatory device. More specifically, the present invention relates to apparatus for supporting a stimulatory device to facilitate and/or maximize stimulation such as genital stimulation.

Apparatus have been created to support stimulatory devices such as vibrators in a vertical position. One such apparatus includes a suction cup for supporting the vibrator atop a horizontal surface. Such suction cup is coupled to the downwardly facing surface of a holding cup into which a vibrator may be removeably inserted. The suction cup allows the vibrator to be supported in a vertical position atop any rigid surface conducive to attachment of a suction cup. Such vertical positioning allows a user to straddle the vibrator and/or insert the vibrator into the vagina for stimulation of the vaginal areas. Additionally, the means for coupling the suction cup to the holding cup allows the holding cup, and thus the vibrator contained partially therein, to pivot during use to facilitate and/or maximize stimulation.

In another such system, stimulatory devices such as massagers, vibrators, and the like are supported in a vertical position. In one such system, the base of an elongated vibrator is attached atop an arced plastic base such that the vibrator is maintained in a vertical position. The vibrator is controlled via a remote control for stimulation of internal and external vaginal areas. A user may regulate both vibration and rotation of the vibrator to facilitate and/or maximize stimulation.

Similarly, apparatus have been created to support stimulatory devices such as vibrators, massagers, and the like in a horizontal position. In one such system, the base of an elongated massager is attached to an approximately vertical support surface such that the massager is horizontally positioned. The sliding attachment mechanism allows a user to adjust the height of the massager relative to the vertical support surface. The vertical support surface includes a hinged stand for maintaining the support surface in a vertical position atop a horizontal surface. The horizontal positioning of the massager is designed to allow a user who is kneeling on the horizontal surface with palms placed atop the horizontal surface to back up to the massager for stimulation of the vaginal areas and/or insertion of the vibrator into the vagina for stimulation of the vaginal areas. The ability to adjust the height of the massager accommodates users of varying physical dimensions.

BRIEF SUMMARY OF THE INVENTION

Briefly stated, in one aspect of the present invention, an apparatus for supporting a stimulatory device is provided. The apparatus includes at least one base, at least one recess in an upwardly facing surface of the at least one base, and at least one bore coupled to the recess, wherein the apparatus is configured to support a stimulatory device via placement of at least a portion of a stimulatory device into at least one of the group consisting of the bore, the recess, and combinations thereof.

In another aspect of the present invention, an apparatus for supporting a stimulatory device is provided. The apparatus includes at least one base fabricated from a material selected from the group consisting of a conventional foam, filled conventional foam, high resiliency foam, combustion modified high resiliency foam, modified high resiliency foam, melamine modified foam, and combinations thereof, and at least one recess in an upwardly facing surface of the at least one base, wherein the apparatus is configured to support a stimulatory device via placement of at least a portion of a stimulatory device into the recess.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments that are presently preferred. It should be understood, however, that the invention is not limited to the precise arrangements and instrumentalities shown. In the drawings.

DETAILED DESCRIPTION OF THE INVENTION

Figure 1:
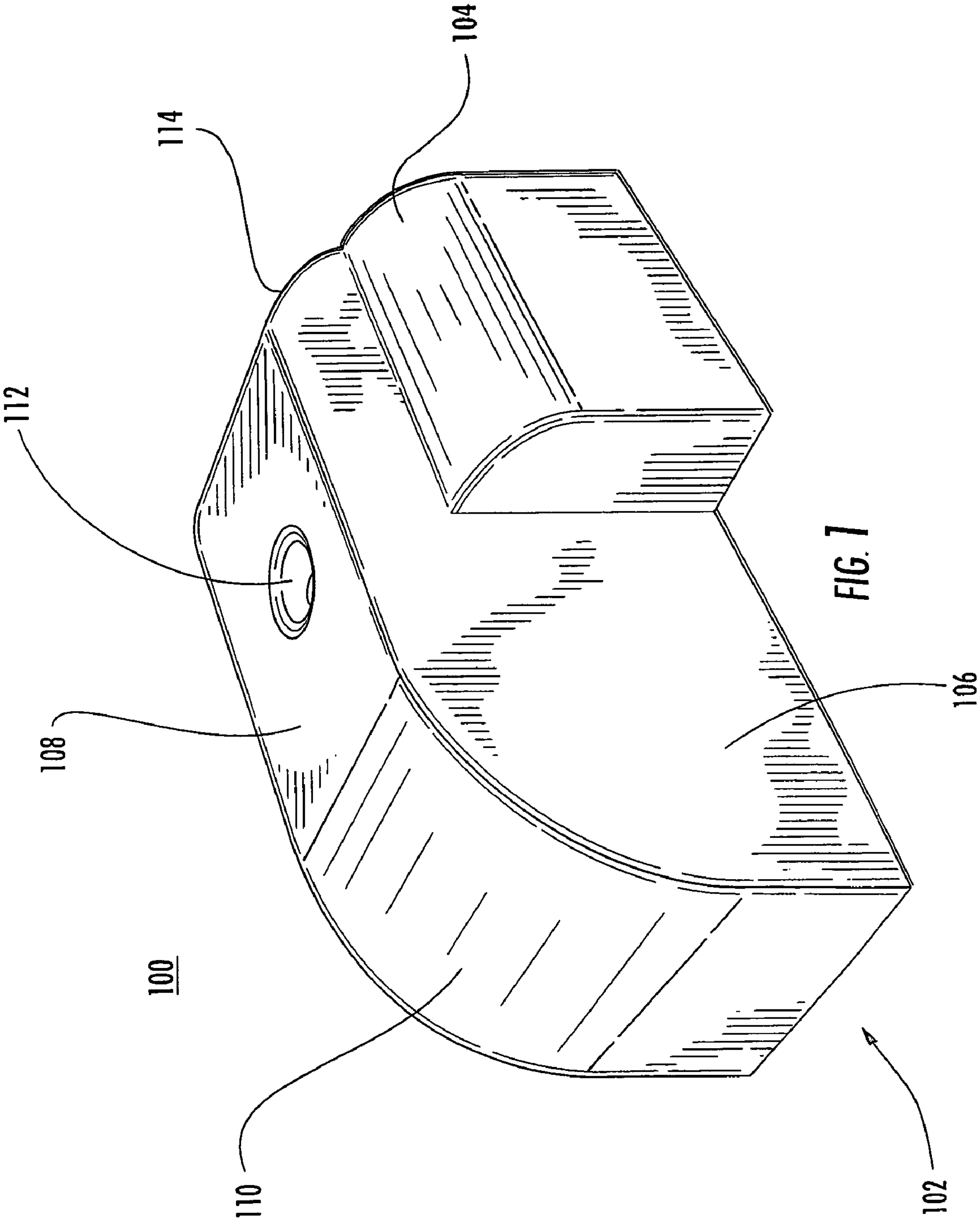
FIG. 1 depicts an angled front view of a stimulatory device support apparatus in accordance with one embodiment of the present invention.

Referring first to FIG. 1, depicted is stimulatory device support apparatus 100 in accordance with one embodiment of the present invention. Stimulatory device support apparatus 100 includes, inter alia, base 102, bolsters 104, sides 106, seat 108, first end 110, recess 112, and second end 114.

Stimulatory device support apparatus 100 may be fabricated from any soft, durable material. In one aspect of the present invention, stimulatory device support apparatus 100 is manufactured from a polymer such as polyurethane foam. Alternatively, stimulatory device support apparatus 100 may be manufactured from other foams such as conventional foam, filled conventional foam, high resiliency foam, combustion modified high resiliency foam, modified high resiliency foam, or melamine modified foams.

Fabrication of stimulatory device support apparatus 100 from a material such as foam allows a user to comfortably straddle a stimulatory device such as a massager, vibrator, or the like mounted in stimulatory device support apparatus 100 by simply sitting atop seat 108. Consequently, a user is not required to support her weight, which relieves stress and/or tension for the user and maximizes her enjoyment and/or the stimulatory effects of the stimulatory device. Furthermore, the ability of the user to rest her weight atop stimulatory device support apparatus 100 minimizes fatigue, thereby allowing prolonged use of the device. Additionally, the use of a yielding material such as foam increases the comfort and ease of movement of a user about the apparatus while simultaneously increasing the safety of the device by minimizing the potential for abrasions or injury to the user's skin when straddling or otherwise using stimulatory device support apparatus 100. However, materials other than foam may be substituted without departing from the scope of the present invention.

Preferably stimulatory device support apparatus 100 is fabricated from a single unit of material such as foam to minimize the possibility of breakage or damage during use. However, stimulatory device support apparatus 100 may be fabricated by coupling a plurality of units without departing from the scope of the present invention. In one aspect of the present invention, bolsters 104 are glued or otherwise affixed to base 102 as part of an assembly process.

The configuration of base 102 accommodates placement of stimulatory device support apparatus 100 on any horizontal surface. In the embodiment of the present invention depicted in FIG. 1, base 102 of stimulatory device support apparatus 100 (excluding bolsters 104) is approximately fourteen inches long, approximately five inches wide, and approximately seven and one quarter inches high (at its highest dimension). However, bases having varying dimensions may be substituted without departing from the scope of the present invention. For example, stimulatory device support apparatus 100 may be fabricated in a travel size in which one or more of the dimensions of stimulatory device support apparatus 100 are decreased. Alternatively, stimulatory device support apparatus 100 may be fabricated for large or tall users in which one or more of the dimensions of stimulatory device support apparatus 100 are increased.

In one aspect of the present invention, bolsters 104 extend from both sides 106 of base 102 to provide stability to stimulatory device support apparatus 100 during use on a horizontal surface. Furthermore, bolsters 104 increase the structural integrity of stimulatory device support apparatus 100. That is, inclusion of one or more bolsters 104 prevents stimulatory device support apparatus 100 from deflecting and/or collapsing during use. In the embodiment of the present invention depicted in FIG. 1, the upwardly facing surface of bolsters 104 is tapered such that a user may comfortably rest her legs, buttocks, or the like atop bolsters 104 when sitting or lying atop stimulatory device support apparatus 100. Additionally, bolsters 104 allow a user to hold stimulatory device support apparatus 100 in place during use as described in greater detail below.

Varying bolster configurations and quantities may be substituted for bolsters 104. For example, bolsters may include specifically configured indentations designed to conform to the user's legs, buttocks, or the like. Or, such bolsters may be designed to accommodate secure placement of the user's legs via the use of ties, straps, or the like. Furthermore, the height of the bolsters may equal the height of sides 106 of base 102 to extend the area of seat 108. In the embodiment of the present invention depicted in FIG. 1, each bolster 104 is approximately two inches wide; therefore, the resultant width of seat 108 would be approximately nine inches. However, varying dimensions, configurations, and quantities of the bolsters may be substituted without departing from the spirit of the present invention.

In one aspect of the present invention, seat 108 is located on the upwardly facing surface of base 102. Seat 108 allows a user to rest atop stimulatory device support apparatus 100 in any one of a plurality of positions such as seated, reclined, prone, and the like for use of the device as described in greater detail below.

In one aspect of the present invention such as that depicted in FIG. 1, recess 112 is recessed within seat 108. Although recess 112 is depicted in FIG. 1 as approximately centrally located within seat 108, other locations of recess 112 may be substituted without departing from the spirit of the present invention. For example, recess 112 may be located in first end 110 of base 102. First end 110 extends from the perimeter of seat 108 to the bottom edge of base 102 within sides 106 of base 102 as a smooth, uninterrupted surface to minimize the possibility of abrasions or other injuries to the user. However, the location of recess 112 of the present invention is not so limited.

Recess 112, as well as bore 302 (FIG. 3) and tapered bore outlet 402 (FIG. 4), facilitate placement and positioning of a stimulatory device such as a massager, vibrator, or the like within stimulatory device support apparatus 100. In the depicted embodiment, recess 112 extends approximately two inches below the upwardly facing surface of stimulatory device support apparatus 100. Recess 112 is coupled to bore 302 (FIG. 3) to allow varying lengths of the stimulatory device to extend beyond seat 108. For example, in one use of stimulatory device support apparatus 100, the stimulatory device is positioned in recess 112 and bore 302 such that the head of the stimulatory device only extends above seat 108. In another use of stimulatory device support apparatus 100, the base of the stimulatory device is seated within recess 112 only such that the entire stimulatory device (other than that contained within recess 112) extends beyond seat 108. However, stimulatory devices may be otherwise positioned without departing from the scope of the present invention. Also, other embodiments of the present invention having one or more recesses 112 of similar or varying depths and/or locations may be substituted without departing from the scope hereof. In some such embodiments, recesses 112 may be formed, sized, or otherwise configured to accommodate specific stimulatory device manufacturers, models, sizes, and the like.

After placement of a stimulatory device within stimulatory device support apparatus 100, a user may rest atop stimulatory device support apparatus 100 in any one of a plurality of positions such as seated, reclined, prone, and the like to use the stimulatory device with the present invention. In one such use of the present invention, a user sits atop seat 108 facing first end 110 such that the user's vagina, clitoris, or the like may easily contact the stimulatory device. Such positioning also allows the user to stabilize stimulatory device support apparatus 100 by applying inwardly directed pressure to bolsters 104 with the user's legs, feet, or the like. Furthermore, when stimulatory device support apparatus 100 is used in such a position, the user may rest her buttocks, legs, or the like atop bolsters 104 such that she is not required to entirely support her weight. That is, stimulatory device support apparatus 100 at least partially supports her weight, which may relieve stress and/or tension for the user and may therefore maximize her enjoyment and/or the stimulatory effects of the stimulatory device (e.g., a user may achieve sexual stimulation and/or one or more orgasms). Furthermore, the ability of the user to at least partially rest her weight atop stimulatory device support apparatus 100 minimizes fatigue, thereby allowing prolonged use of the device. However, other positioning of a user with respect to stimulatory device support apparatus 100 may be substituted without departing from the scope hereof.

The depth and angled nature of recess 112 and/or bore 302, as depicted in greater detail below with respect to FIG. 5, allow a stimulatory device such as a massager to be positioned such that a vibrating portion thereof (e.g., a vibrating head) easily contacts the user's genitalia. Consequently, the positioning of the stimulatory device within recess 112 and/or bore 302 relative to seat 108 allows a user seated atop seat 108, or straddling seat 108, to easily adjust her position by leaning, rolling, or the like such that the amount of pressure applied to her genitalia by the stimulatory device, as well as the portion of the genitalia in contact with the stimulatory device, may be easily varied. Such adjustments allow a user to maximize the stimulative effects of the stimulatory device.

In another aspect of the present invention, the ability of the user to rest atop stimulatory device support apparatus 100 in any one of a plurality of positions such as seated, reclined, prone, and the like frees the user's hands during use of stimulatory device support apparatus 100. Since the stimulatory device support apparatus 100 eliminates the need for the user to hold the stimulatory device, the user is therefore free to use her hands for massage or simulation of other parts of her body or her partner's body, thereby increasing either partner's stimulation level and the overall experience of the user and/or her partner that results from use of stimulatory device support apparatus 100. Furthermore, the stimulatory device support apparatus 100's ability to hold the stimulatory device in a stationary position allows a user to adjust the pressure and position of the stimulatory device relative to the genitalia without the use of her hands (i.e., simply by moving her body relative to the stationary stimulatory device) potentially increasing the ease of use and overall enjoyment of the stimulatory device.

Although a solitary user may use stimulatory device support apparatus 100, it is also designed for use during sexual intercourse between two individuals (e.g., a user and her partner). In one such use of the present invention, a user leans forward over stimulatory device support apparatus 100 in any one of a number of positions such that one or more genital areas are in contact with the stimulatory device. Simultaneously, the user's partner penetrates the user from a rearward position. However, other methods of using stimulatory device support apparatus 100 during sexual intercourse may be substituted without departing from the scope of the present invention. The angled nature of first end 110 and second end 114 minimize the possibility that stimulatory device support apparatus 100 will be obtrusive and/or cause injury to the user or her partner when such apparatus is used during sexual intercourse.

Although stimulatory device support apparatus 100 may be used recreationally or therapeutically, the present invention is not so limited. Stimulatory device support apparatus 100 may be prescribed or recommended during counseling for sexual dysfunction. A psychiatrist, psychologist, doctor, or the like may recommend use of stimulatory device support apparatus 100 or may provide his or her patients with specific instructions for using a particular embodiment of the present invention to combat her particular sexual dysfunction. Alternatively, a couple may choose to use stimulatory device support apparatus 100 to combat sexual dysfunction without the recommendation of a psychiatrist, psychologist, doctor, or the like.

Figure 2:
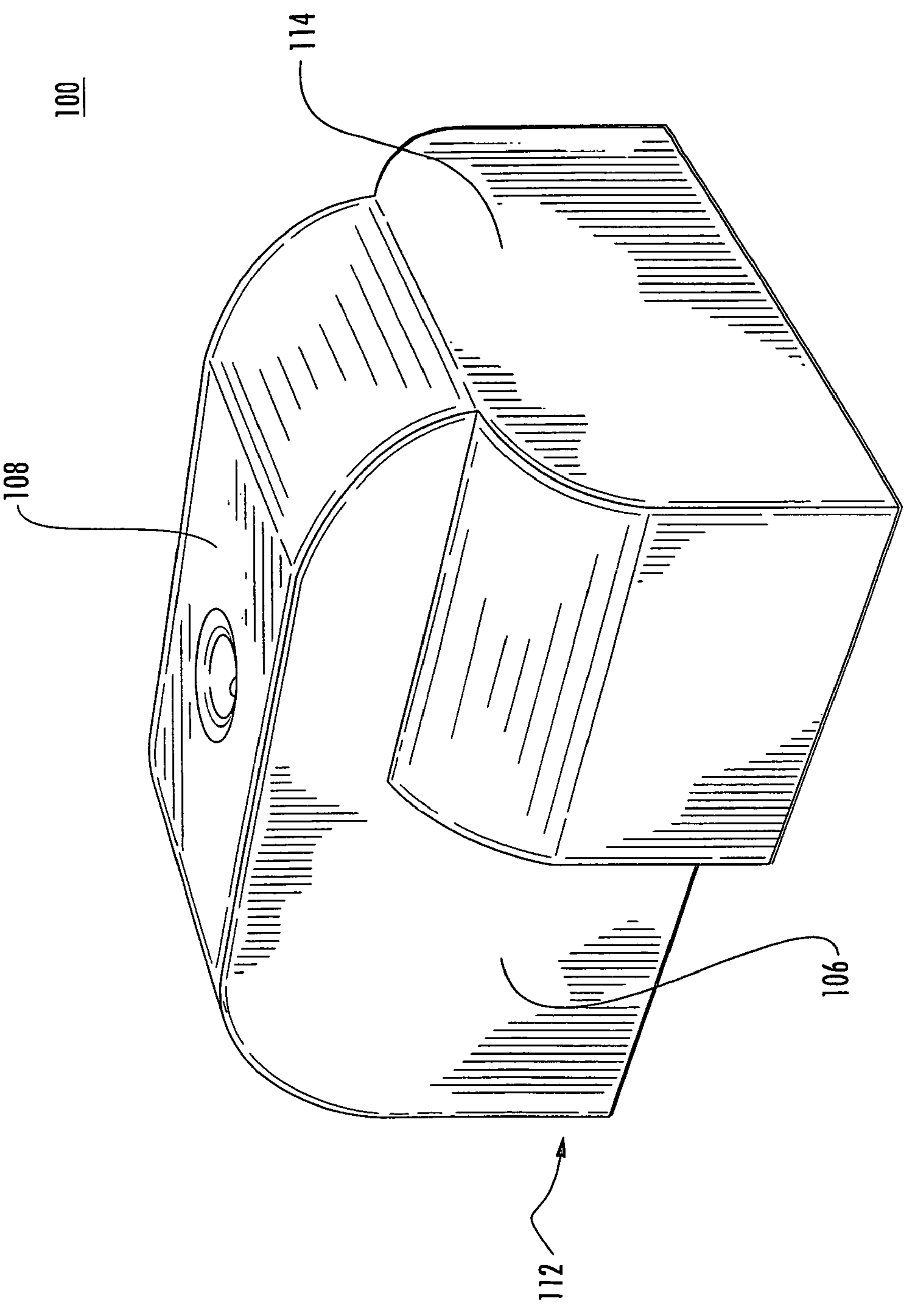
FIG. 2 depicts an angled back view of a stimulatory device support apparatus in accordance with the embodiment of the present invention depicted in FIG. 1.

Turning next to FIG. 2, depicted is an angled view depicting second end 114 of stimulatory device support apparatus 100 in accordance with one embodiment of the present invention. Second end 114 extends from the perimeter of seat 108 to the bottom edge of base 102 within sides 106 of base 102 as a smooth, uninterrupted surface to minimize the possibility of abrasions or other injuries to the user. The tapered nature of second end 114 also allows a user to comfortably straddle or rest atop stimulatory device support apparatus 100. However, other configurations of second end 114 may be substituted without departing from the scope hereof. During use of stimulatory device support apparatus 100, a user may face first end 110, second end 114, or either side 106 without departing from the scope of the present invention.

Figure 3:
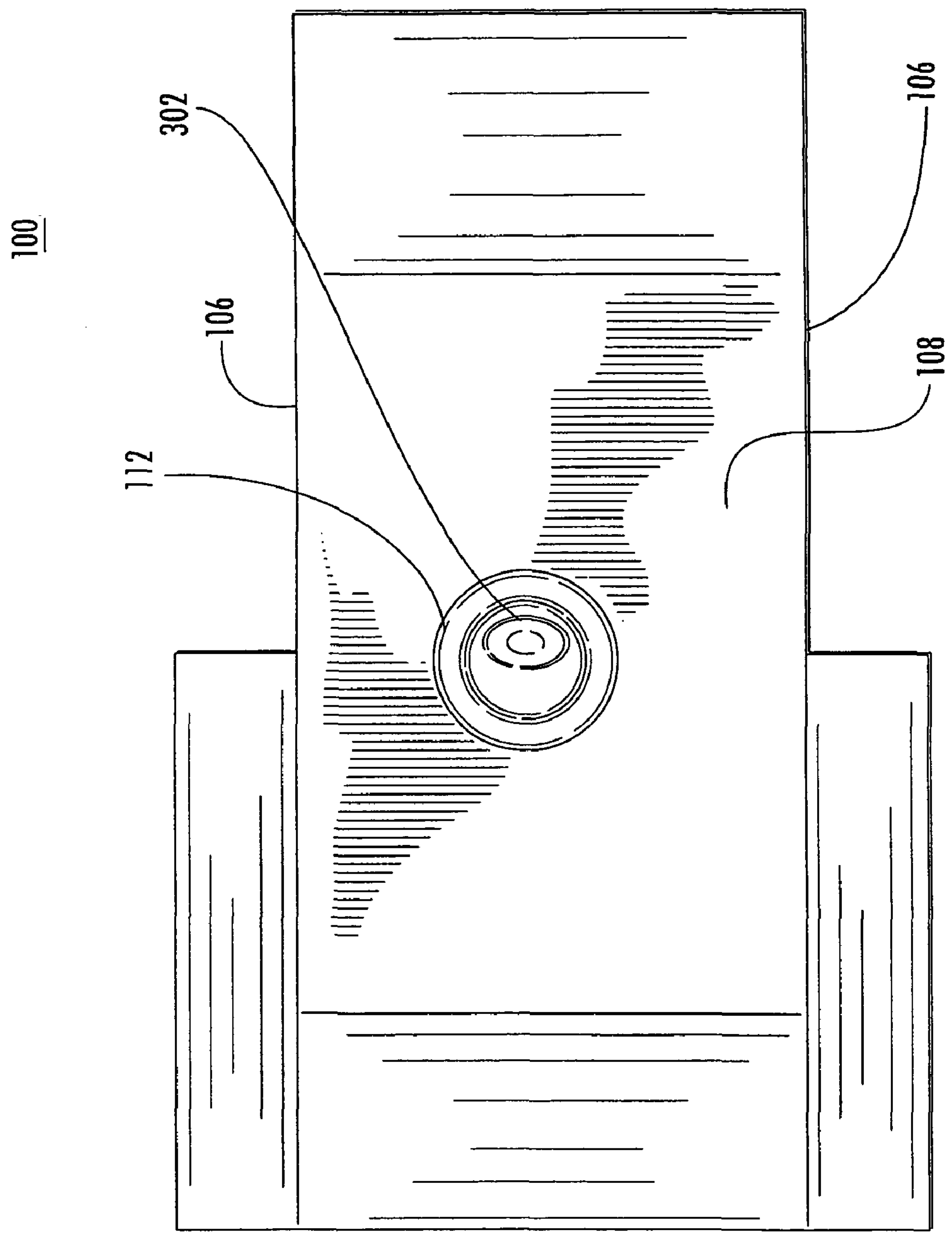
FIG. 3 depicts a top view of a stimulatory device support apparatus in accordance with the embodiment of the present invention depicted in FIG. 1.

Referring next to FIG. 3, depicted is a top view of stimulatory device support apparatus 100 in accordance with one embodiment of the present invention. Recess 112 is approximately centered within seat 108 and between sides 106 of stimulatory device support apparatus 100. A stimulatory device such as a massager, vibrator, or the like may be inserted in and/or supported by recess 112 and/or bore 302 until the desired length of the massager, vibrator, or the like extends above the upwardly facing surface of seat 108. In one aspect of the present invention, the stimulatory device is a Hitachi Magic Wand. However, the present invention is not so limited.

Bore 302 is coupled to recess 112. In one aspect of the present invention, bore 302 is coupled at an approximately 135-degree angle relative to the axis of recess 302. In another aspect of the present invention, the diameter of bore 302 is sized such that its inwardly facing surfaces exert pressure on outwardly facing surfaces of the stimulatory device, whenever such stimulatory device is inserted into bore 302. That is, the diameter of bore 302 is less than the diameter of the compatible stimulatory devices, however, the yielding nature of the material of base 102 allows the stimulatory device to be inserted therein and thereafter maintained in a stationary position.

For non-battery powered devices, bore 302 also facilitates stringing of the electrical cord through stimulatory device support apparatus 100 as discussed in greater detail below with respect to FIG. 5 to facilitate use of the apparatus, to prevent entanglement with the electrical cord, and to minimize the possibility of injury caused by such electrical cord. However, embodiments of the present invention are envisioned in which bore 302 are eliminated and/or otherwise configured.

The central location of recess 112 allows a user to use stimulatory device support apparatus 100 in virtually any position without adjusting the position of the stimulatory device. To further accommodate such use, the length of seat 108 is extended by the tapered portions of first end 110 and second end 114 to facilitate resting comfortably in any manner and in any direction atop stimulatory device support apparatus 100. However, other locations for recess 112 and/or bore 302 may be substituted without departing from the scope of the present invention.

Figure 4:
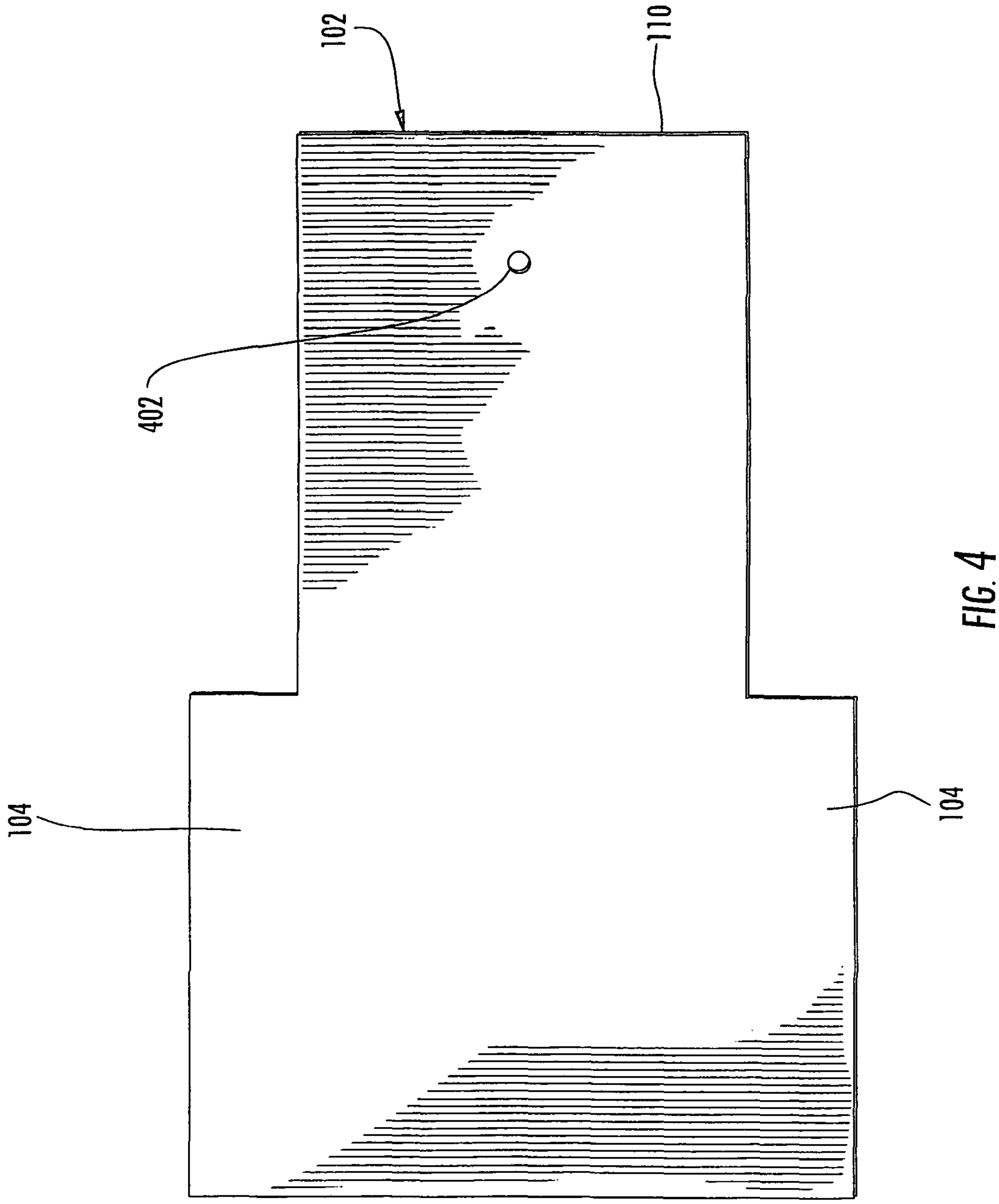
FIG. 4 depicts a bottom view of a stimulatory device support apparatus in accordance with the embodiment of the present invention depicted in FIG. 1.

Turning next to FIG. 4, depicted is a bottom view of stimulatory device support apparatus 100 in accordance with one embodiment of the present invention. The bottom of stimulatory device support apparatus 100 includes the bottoms of base 102 and bolsters 104. Also depicted is bore outlet 402 of bore 302 (i.e., the portion of bore 302 that penetrates the downwardly facing surface of stimulatory device support apparatus 100). As depicted in greater detail in FIG. 5, bore 302 is angled such that bore outlet 402 is located towards first end 110 of stimulatory device support apparatus 100 whereas the opposing outlet of bore 302 is coupled to recess 112, which is approximately centered within seat 108 and is therefore located closest to second end 114. The angled nature of bore 302, as well as the location of bore outlet 402 minimizes the effect of an electrical cord strung throughout stimulatory device support apparatus 100 upon the stability of stimulatory device support apparatus 100 by minimizing the contact between the bolster-stabilized end of stimulatory device support apparatus 100 and the electrical cord.

Figure 5:
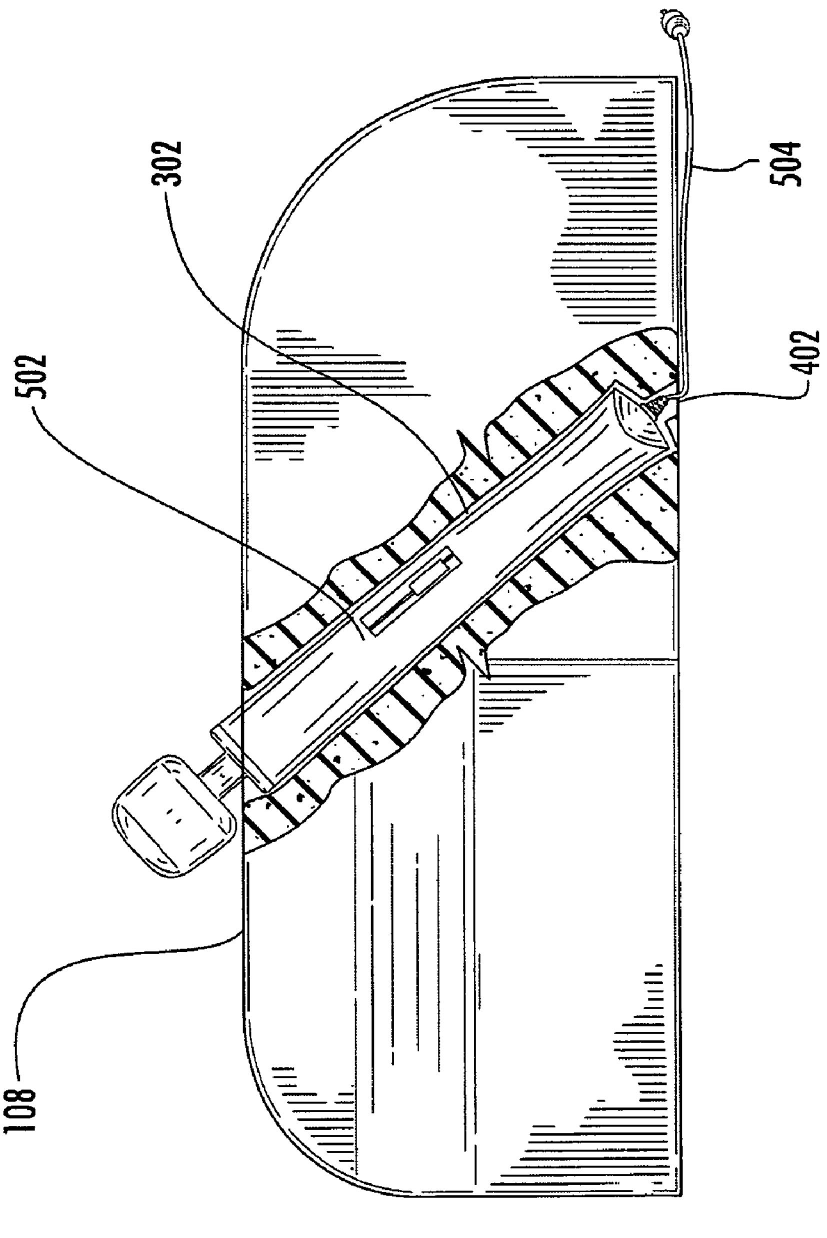
FIG. 5 depicts a cutaway side view of a stimulatory device supported by a stimulatory device support apparatus in accordance with the embodiment of the present invention depicted in FIG. 1.

Referring now to FIG. 5, depicted is a cutaway view of stimulatory device support apparatus 100 with stimulatory device 502 removeably inserted into and/or supported by recess 112 and bore 302 in accordance with one embodiment of the present invention. To insert stimulatory device 502 into stimulatory device support apparatus 100, electrical cord 504 is first inserted into recess 112. Electrical cord 504 is then threaded through bore 302 until it passes through bore outlet 402. Manufacturing stimulatory device support apparatus 100 from a pliable material such as foam facilitates threading of electrical cord 504 through bore 302. Since stimulatory device support apparatus 100 is flexible, it will easily contract when a light force is applied and will easily expand when such light force is removed.

Once electrical cord 502 has been threaded through bore 302, stimulatory device 502 may then be inserted into recess 112 and/or bore 302 until a desired length of stimulatory device 502 extends above the upwardly facing surface of seat 108. Stimulatory device 502 may then be adjusted within recess 112 and/or bore 302 until the desired position of stimulatory device 502 is achieved. Use of a resilient and pliable material for fabrication of stimulatory device support apparatus 100, as well as the diameter of bore 302, maintains the desired position of stimulatory device 502 after adjustment by the user. Additionally, the use of such a material and/or the size of the diameter of bore 302 allows a variety of stimulatory devices 502 having different shapes, sizes, and the like to be used interchangeably with one stimulatory device support apparatus 100. However, the present invention may be manufactured from non-resilient and/or non-pliable materials without departing from the scope of the present invention. In addition, the present invention may be manufactured with other mechanisms for supporting the stimulatory device in a stationary position such as clips, straps, and the like. For example, embodiments of the present invention are envisioned in which the stimulatory device support apparatus is specifically configured for use with a particular stimulatory device.

Although the present invention has been discussed herein for use by a female, the present invention is not so limited. The depicted embodiments and alternate embodiments discussed herein, as well as those not discussed in detail herein, may also be used by a male.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An apparatus for supporting a stimulatory device comprising:

at least one base;

at least one recess in an upwardly facing surface of the at least one base; and at least one bore coupled to the recess; wherein the apparatus is configured to support a stimulatory device via placement of at least a portion of a stimulatory device into at least one of the bore and/or the recess, wherein the recess is sized to receive a head or a portion of a base of a stimulatory device, and wherein the bore has a diameter that is sized such that inwardly facing surfaces of the bore are capable of exerting pressure on outwardly facing surfaces of a stimulatory device upon insertion of a stimulatory device into the bore; and wherein the pressure retains a stimulatory device therein.

2. The apparatus according to claim 1, wherein the apparatus is configured such that a depth of insertion of a stimulatory device into said the bore and/or the recess may be varied to accommodate variations in a height of a stimulatory device above the upwardly facing surface.

3. The apparatus according to claim 1, further comprising:

at least one bolster coupled to the base; wherein inclusion of the at least one bolster provides at least one of increased stability and/or increased structural integrity.

4. The apparatus according to claim 3, wherein the at least one side bolster includes a tapered upwardly facing surface to allow a user to rest comfortably on top of the side bolster.

5. The apparatus according to claim 1, wherein the at least one bore passes through a downwardly facing surface of the base.

6. The apparatus according to claim 5, wherein the at least one bore of the apparatus has an outlet and is configured to allow a cord of a stimulatory device to be threaded through the apparatus.

7. The apparatus according to claim 1, wherein the upwardly facing surface of the at least one base forms a seat configured for wholly or partially supporting a user.

8. The apparatus according to claim 7, wherein the recess and/or the bore allow for variation in positioning of a stimulatory device so that leaning forward on top of the apparatus allows a user to engage in sexual intercourse while using a stimulatory device and the apparatus.

9. The apparatus according to claim 1, wherein the apparatus is fabricated from a material selected from the group consisting of a conventional foam, filled conventional foam, high resiliency foam, combustion modified high resiliency foam, modified high resiliency foam, melamine modified foam, and combinations thereof.

10. The apparatus according to claim 1, wherein the recess and/or the bore is angled such that a stimulatory device inserted therein contacts at least a portion of genitalia of a user of the apparatus when a user is positions on top of the apparatus.

11. The apparatus according to claim 1, wherein the material of the base is yielding to provide at least one of minimization of abrasions to a user of the apparatus, minimization of injuries to a user, ease of movement of a user about the apparatus and/or comfort to a user.

12. A combination device for use in providing supported use of a stimulatory device to a user comprising:

(i) a support apparatus for supporting a stimulatory device comprising:

at least one base;

at least one recess in an upwardly facing surface of the at least one base; and at least one bore coupled to the recess; and (ii) a stimulatory device at least partially and removably located within the bore and/or the recess, wherein the apparatus is configured to support the stimulatory device via placement of a least a portion of the stimulatory device into at least one of the bore and/or the recess, wherein the recess is sized to receive a head or a portion of a base of the stimulatory device, and wherein the bore has a diameter that is sized such that inwardly facing surfaces of the bore are capable of exerting pressure on outwardly facing surfaces of a stimulatory device upon insertion of a stimulatory device into the bore; and wherein the pressure retains a stimulatory device therein.

13. The combination device according to claim 12, wherein the at least one base of the support apparatus comprises a material selected from the group consisting of a conventional foam, filled conventional foam, high resiliency foam, combustion modified high resiliency foam, modified high resiliency foam, melamine modified foam, and combinations thereof.

14. The combination device according to claim 12, further comprising at least one bolster coupled to the at least one base of the support apparatus, wherein inclusion of the at least one bolster provides increased stability and/or increased structural integrity to the support apparatus.

15. The combination device according to claim 14, wherein the at least one bolster is on a side of the base and the bolster includes a tapered upwardly facing surface to allow a user to rest comfortably on top of the bolster.

16. The combination device according to claim 15, wherein the upwardly facing surface forms a seat for wholly or partially supporting a user.

17. The combination device according to claim 15, wherein the device allows for hands-free operation of the stimulatory device.

18. The combination device according to claim 12, wherein the at least one base comprises a material that is yielding to provide at least one of minimization of abrasions to a user from the support apparatus, minimization of injuries to a user from the support apparatus, ease of movement of a user about the support apparatus and/or comfort to a user.

19. A method of using a stimulatory device, comprising:

(a) providing a support apparatus for supporting a stimulatory device, the support apparatus comprising: at least one base; at least one recess in an upwardly facing surface of the at least one base; and at least one bore coupled to the recess, wherein the recess is sized to receive a head or a portion of a base of a stimulatory device and wherein the bore has a diameter that is sized such that inwardly facing surfaces of the bore are capable of exerting pressure on outwardly facing surfaces of a stimulatory device upon insertion of a stimulatory device into the bore; and wherein the pressure retains a stimulatory device therein;

(b) inserting a stimulatory device at least partially within the bore and/or the recess of the support apparatus so that the support apparatus supports the stimulatory device; and (c) positioning a user on top of the support apparatus so that the user contacts the stimulatory device.

20. The method according to claim 19, further comprising repositioning of the user on top of the support apparatus so that the user can alter at least one of a pressure and/or a position of the stimulatory device.

21. The method according to claim 19, wherein the user may operate the stimulatory device in a hands-free manner by using the support apparatus with the stimulatory device inserted therein.

22. The method according to claim 19, wherein the stimulatory device comprises an electrical cord and the at least one bore has an outlet, and the method further comprises threading the electrical cord through the bore so that an end of the electrical cord extends out from the outlet in the at least one bore.

23. A combination device for use in providing supported use of a stimulatory device to a user comprising:

(i) a support apparatus for supporting a stimulatory device comprising:

at least one base;

at least one recess in an upwardly facing surface of the at least one base;

at least one bore coupled to the recess; and at least one bolster coupled to the at least one base of the support apparatus, wherein inclusion of the at least one bolster provides increased stability and/or increased structural integrity to the support apparatus, the at least one bolster is on a side of the base and the bolster includes a tapered upwardly facing surface to allow a user to rest comfortably on top of the bolster; and (ii) a stimulatory device at least partially and removably located within the bore and/or the recess, wherein the apparatus is configured to support the stimulatory device via placement of a least a portion of the stimulatory device into at least one of the bore and/or the recess, and wherein the recess is sized to receive a head or a portion of a base of the stimulatory device.

24. The combination device according to claim 23, wherein the at least one base of the support apparatus comprises a material selected from the group consisting of a conventional foam, filled conventional foam, high resiliency foam, combustion modified high resiliency foam, modified high resiliency foam, melamine modified foam, and combinations thereof.

25. The combination device according to claim 23, wherein the upwardly facing surface forms a seat for wholly or partially supporting a user.

26. The combination device according to claim 23, wherein the device allows for hands-free operation of the stimulatory device.

27. The combination device according to claim 23, wherein the at least one base comprises a material that is yielding to provide at least one of minimization of abrasions to a user from the support apparatus, minimization of injuries to a user from the support apparatus, ease of movement of a user about the support apparatus and/or comfort to a user.

28. A method of using a stimulatory device, comprising:

(a) providing a support apparatus for supporting a stimulatory device, the support apparatus comprising: at least one base; at least one recess in an upwardly facing surface of the at least one base; and at least one bore coupled to the recess, wherein the recess is sized to receive a head or a portion of a base of a stimulatory device, and wherein the stimulatory device comprises an electrical cord and the at least one bore has an outlet;

(b) inserting a stimulatory device at least partially within the bore and/or the recess of the support apparatus so that the support apparatus supports the stimulatory device;

(c) threading the electrical cord through the bore so that an end of the electrical cord extends out from the outlet in the at least one bore; and (d) positioning a user on top of the support apparatus so that the user contacts the stimulatory device.

29. The method according to claim 28, further comprising repositioning of the user on top of the support apparatus so that the user can alter at least one of a pressure and/or a position of the stimulatory device.

30. The method according to claim 28, wherein the user may operate the stimulatory device in a hands-free manner by using the support apparatus with the stimulatory device inserted therein.

* * * * *